US012220472B2

(12) United States Patent
Breakspear et al.

(10) Patent No.: US 12,220,472 B2
(45) Date of Patent: *Feb. 11, 2025

(54) PROCESS FOR RESHAPING KERATIN FIBERS

(71) Applicant: KAO GERMANY GMBH, Darmstadt (DE)

(72) Inventors: Steven Breakspear, Darmstadt (DE); Niu Jian, Darmstadt (DE); Bernd Nöcker, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 488 days.

This patent is subject to a terminal disclaimer.

(21) Appl. No.: 17/299,208

(22) PCT Filed: Dec. 3, 2019

(86) PCT No.: PCT/EP2019/083525
§ 371 (c)(1),
(2) Date: Jun. 2, 2021

(87) PCT Pub. No.: WO2020/115060
PCT Pub. Date: Jun. 11, 2020

(65) Prior Publication Data
US 2022/0133613 A1 May 5, 2022

(30) Foreign Application Priority Data
Dec. 6, 2018 (EP) ..................................... 18210805

(51) Int. Cl.
*A61K 8/41* (2006.01)
*A61K 8/19* (2006.01)
*A61K 8/34* (2006.01)
*A61K 8/73* (2006.01)
*A61Q 5/04* (2006.01)

(52) U.S. Cl.
CPC .................. *A61K 8/41* (2013.01); *A61K 8/19* (2013.01); *A61K 8/345* (2013.01); *A61K 8/732* (2013.01); *A61Q 5/04* (2013.01); *A61K 2800/48* (2013.01); *A61K 2800/805* (2013.01); *A61K 2800/88* (2013.01)

(58) Field of Classification Search
CPC . A61K 8/41; A61K 8/19; A61K 8/345; A61K 8/732; A61K 2800/48; A61K 2800/805; A61K 2800/88; A61K 2800/30; A61K 8/42; A61K 8/73; A61K 8/8152; A61Q 5/04
USPC .......................................................... 424/702
See application file for complete search history.

(56) References Cited

U.S. PATENT DOCUMENTS

| | | | |
|---|---|---|---|
| 1,985,424 A | 12/1934 | Piggott | |
| 2,016,962 A | 10/1935 | Flint et al. | |
| 2,703,798 A | 3/1955 | Schwartz | |
| 11,324,685 B2 * | 5/2022 | Nöcker | A61Q 5/04 |
| 2012/0093755 A1 * | 4/2012 | Humphreys | A61K 8/35 424/70.14 |
| 2013/0146080 A1 * | 6/2013 | Colaco | A61Q 5/06 424/70.11 |
| 2014/0261517 A1 * | 9/2014 | Humphreys | A61K 8/19 132/204 |
| 2016/0296449 A1 * | 10/2016 | Kadir | A61Q 5/06 |

FOREIGN PATENT DOCUMENTS

| | | | |
|---|---|---|---|
| CN | 103260595 A | 8/2013 | |
| EP | 70 074 A2 | 1/1983 | |
| JP | 2015-123019 A | 8/1995 | |
| WO | 92/06984 A1 | 4/1992 | |
| WO | 96/27366 A1 | 9/1996 | |
| WO | 2011/1004505 A | 1/2011 | |
| WO | WO-2011155076 A1 * | 12/2011 | ............... A61K 8/19 |
| WO | 2019/074128 A2 | 4/2019 | |

OTHER PUBLICATIONS

Yanhong et al., Common Knowledge "Comprehensive design experiments in Chemistry", Textbook for Higher Education, Central University for Nationalities Publishing, Mar. 2018.
International Search Report dated Feb. 24, 2020, in connection with PCT International Application No. PCT/EP2019/083525.

\* cited by examiner

*Primary Examiner* — Isaac Shomer
*Assistant Examiner* — Bryan James Rego
(74) *Attorney, Agent, or Firm* — Norris Mclaughlin, P.A.

(57) ABSTRACT

Processes and kits-of-parts reshape keratin fibers and comprise applying a composition on to keratin fibers and cover the keratin fibers, wherein the composition comprise an alkalizing agent, a thickening polymer, and an organic solvent. Additionally, the keratin fibers are put under tension using a curler along with covering the curler with a moisture barrier, and heating the keratin fibers. As a result, long-lasting curl having cosmetic properties are achievable.

8 Claims, No Drawings

PROCESS FOR RESHAPING KERATIN FIBERS

This application is the U.S. National Stage of International Application No. PCT/EP2019/083525, filed Dec.. 3, 2019, which claims foreign priority benefits under 35 U.S.C. § 119 of European Application No. 18210805.0, filed Dec. 6, 2018, the disclosure of which is incorporated herein by reference.

FIELD OF THE INVENTION

The present invention relates to a process for reshaping keratin fibers comprising a reshaping composition and a moisture barrier.

BACKGROUND OF THE INVENTION

Current permanent reshaping processes require steps of reducing the hair and later oxidizing the hair. The reducing step employs reducing agents, such as thioglycolic acid, in order to cleave disulphide bonds within the hair and to allow protein chain movement. In a subsequent step the bonds are reformed by addition of an oxidizing composition, typically comprising hydrogen peroxide. In Western countries these well known processes include cold perming and hot perming techniques, whereas, especially in Asian countries, a digital perming as a specialty of the hot perming process is preferred. For a digital perming process the temperature of the perm is controlled by an electronic device, often being equipped with a microprocessor. These multi-step processes are time-consuming (up to 3 hours for a cold perm/5 hours for a digital perm), require a high level of winding skill from the stylist, cause hair damage and, at worst, can lead to hair loss due to over-processing. Over-processing typically stems from either leaving the reducing agent for too long on the hair, or heating the hair to inappropriate temperatures for a too long time. To avoid over-processing, a test curler is typically carried out on a streak of the client's hair prior to the full process being performed, in order to determine the optimum processing time; this adds further to the time needed and requires further skills/education from the stylist. Apart from all the process challenges, the reducing composition has a strong and acrid odour disliked by stylists and consumers alike.

In contrast to the common reducing techniques, WO2011155076 and WO20111004505 disclose perming processes and compositions which do not make use of reducing or oxidizing agents, but of compositions comprising different alkalizing agents at alkaline pH. However, the documents are silent on the technical effect of a thickening polymer in combination with an organic solvent system.

Despite all efforts of the prior art and the long experience with reducing/oxidizing processes, there is a real need to perming processes which do not show the disadvantages as presented above, improved curling efficiency, and convenient use with minimal risk of errors from the user.

SUMMARY OF THE INVENTION

Therefore, the first object of the present invention is a process for reshaping keratin fibers, preferably human keratin fibers, more preferably human hair characterized in that it comprises the steps of:

a) putting keratin fibers under mechanical tension,
b) applying to keratin fibers a non-reducing, non-oxidizing alkaline composition with a pH in the range of 7 to 12, preferably in the range of 8 to 11, comprising:
  i) one or more alkalizing agent(s),
  ii) one or more thickening polymer(s),
  iii) one or more organic solvent(s) having two or more hydroxyl groups,
c) optionally covering keratin fibers with a moisture barrier,
d) heating the keratin fibers to a temperature in the range of 50° C. to 230° C.,
e) optionally removing the moisture barrier from keratin fibers,
f) releasing tension from keratin fibers,
g) optionally rinsing-off the keratin fibers, wherein process steps a), b), and f), g) can be executed in either order.

The second object of the present invention is a kit-of-parts comprising in a separately packed container an alkaline composition as defined for step b) as defined above, and a moisture barrier as defined above for step c).

DETAILED DESCRIPTION OF THE INVENTION

It has been surprisingly found by the inventors of the present invention that a composition having a pH in the range of 7 to 12 comprising an alkalizing agent as well as a thickening polymer and organic solvent used in a perming process in combination with a moisture barrier delivered superior, long-lasting curling results, and minimal risk of over-processing and low damage of the hair fibers.

Non-Reducing, Non-Oxidizing Alkaline Composition of Step b)

The term 'non-reducing' within the meaning of the present invention is to be understood that the composition of step b) is free of agents causing a reduction of disulfide bonds in the keratin fibers. The term does not exclude low amounts of reducing agents which may be necessary in the composition for stabilizing purposes.

The term 'non-oxidizing' within the meaning of the present invention is to be understood that the composition of step b) is free of oxidizing agents causing an oxidation of disulfide bonds in the keratin fibers. The term does not exclude low amounts of oxidizing agents which may be necessary in the composition for stabilizing purposes.

The composition comprises one or more alkalizing agent(s), from the viewpoint of achieving a sufficiently high pH and good curling result. The preferred pH range is 8 to 11 from the viewpoint of achieving a good curling result in combination with low hair damage.

The composition further comprises one or more alkalizing agent(s) selected from organic alkalizing agent(s) and/or their salts, and/or inorganic alkalizing agents and/or their salt(s).

Suitably, the alkalizing agent of the alkaline composition of step b) is selected from ammonia and/or its salt(s), guanidine and/or its salt(s), and/or organic alkyl and/or alkanol amines according to the general structure

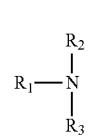

wherein R1, R2, and R3 are independently selected from H, linear C1-C6 alkyl which may be substituted with one hydroxyl group, or branched C3-C12 alkyl or alkanol, wherein at least one of R1, R2, or R3 is different from H, and/or their salts.

The organic alkyl and/or alkanol amine according to the structure above may be selected from mono- and/or diethanolamine, butyl ethanolamine, butyl diethanolamine, dibutyl ethanolamine, methylethanolamine, triethanolamine, N-lauryl diethanolamine, diisopropanolamine, dimethyl isopropanolamine, isopropanolamine, triisopropanolamine, isobutanolamine, tris-(hydroxymethyl)-aminomethane, and/or aminomethyl propanol. Equally suitable are salts of alkyl and/or alkanol amines with a counterion preferably selected from chloride and/or hydrogen chloride, nitrate, sulphate, phosphate, hydrogenphosphate, dihydrogenphosphate, citrate, acetate, sulphite, benzoate, salicylate.

In one aspect of the present invention, the alkalizing agent of the alkaline composition of step b) is selected from aminomethyl propanol and/or monoethanolamine, and/or diethanolamine, and/or tris-(hydroxymethyl)-aminomethane, and/or their salts.

In another aspect of the present invention, the alkalizing agent of the alkaline composition of step b) is ammonia and/or its salts.

In yet another aspect of the present invention, the composition of step b) comprises at least 2 different alkalizing agents. The first alkalizing agent of the alkaline composition of step b) is selected from ammonia and/or its salt(s) and the second alkalizing agent is selected from aminomethyl propanol and/or monoethanolamine, and/or diethanolamine, and/or their salts.

In a most preferred aspect of the present invention the alkalizing agent is a mixture of one or more alkyl amine(s) and/or their salt(s) with ammonia and/or its salt(s). A preferred combination is, for example, monoethanolamine and/or its salt(s) and ammonia and/or its salt(s). Another preferred combination is aminomethyl propanol and/or its salt(s) and ammonia and/or its salt(s). The aforementioned combinations are preferred from the viewpoint of reducing ammonia smell while maintaining good curling performance, and minimal hair damage.

Preferably, the total concentration of alkalizing agent(s) of the alkaline composition of step b) is in the range of 0.1% to 10% by weight, more preferably in the range of 0.25% to 7.5% by weight, further more preferably in the range of 0.5% to 5% by weight, calculated to the total of the composition.

For attaining the above mentioned effects, the preferred total concentration of alkalizing agent(s) in the alkaline composition of step b) is in the range of 0.1% to 10% by weight, preferably in the range of 0.25% to 7.5% by weight, more preferably in the range of 0.5% to 5% by weight, calculated to the total of the composition of step b).

When ammonia is used as alkalizing agent of the composition of step b), the ammonium salts for buffering the composition of step b) may be used, preferably selected from inorganic and/or organic ammonium salts.

Suitable inorganic ammonium salts are preferably selected from ammonium chloride, ammonium sulfate, ammonium carbonate, ammonium hydrogen carbonate, ammonium phosphates, ammonium hydrogen phosphates, ammonium dihydrogen phosphates, ammonium nitrate, ammonium bromide, ammonium iodide, ammonium thiosulfate, ammonium molybdate, ammonium vanadate, and/or their mixtures.

Suitable organic ammonium salts are preferably selected from ammonium carbamate, ammonium sulfamate, ammonium citrate, ammonium salicylate, ammonium valerate, ammonium tartarate, ammonium benzoate, ammonium acetate, ammonium formiate, and ammonium lactate, ammonium salts of polymers, and/or their mixtures.

Preferably, the weight ratio of ammonia to ammonium salt(s) in the alkaline composition of step b) is in the range of 10 to 1.

Thickenering Polymers

Preferably, the polymeric thickener of the alkaline composition of step b) is selected from associative and/or non-associative thickening polymers, and/or their mixtures.

Associative and/or non-associative thickening polymers or more thickening polymers may be anionic, nonionic, cationic or amphoteric polymers, and are preferably selected from polymers resulting in a solution and/or dispersion at pH between 8 and 10 with a viscosity of at least 500 mPa·s measured at a polymer concentration of 1% by weight in water and at 20° C. with a Brookfield viscometer, such as at 10 rpm for 1 min, with an appropriate spindle.

Suitable associative thickening polymers may be anionic thickening polymers, preferably selected from copolymers and/or crosspolymers which comprise an acrylate and/or methacrylate monomer unit and at least one more hydrophobic unit such as alkyl chains. Examples are acrylates/c10-30 alkyl acrylate crosspolymer, acrylates/steareth-20 methacrylate copolymer, acrylates/stearyl acrylate/dimethicone methacrylate copolymer, acrylates/beheneth-25 methacrylate copolymer, acrylates/lauryl acrylate/stearyl acrylate/ethylamine oxide methacrylate copolymer.

Suitable non-ionic associative thickening polymers are, for example, alkyl modified cellulose derivatives such as $(C_2-C_8)$-alkylcellulose.

Suitable non-associative non-ionic thickening polymers are cellulose polymers, preferably methyl cellulose, ethyl cellulose, hydroxyethylcellulose, methylhydroxyethylcellulose, methylhydroxypropylcellulose, or starch based polymers such as vegetable starch and/or their synthetically modified derivatives such as hydroxypropyl starch phosphate.

Suitable non-associative anionic polymers are carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

Suitable cationic non-associative polymers are Polyquaternium 6, Polyquaternium 16, and Polyquaternium 37.

Preferably, the associative thickening polymers of the alkaline composition of step b) are selected from acrylate copolymers being modified with alkyl and/or alkylene chains in the range of of C6 to C30.

Preferably, the non-associative thickening polymers of the alkaline composition of step b) are selected from xanthan gum, dehydroxanthan gum, starch, and hydrophobically modified starch, and/or their mixtures.

Suitably, the total concentration thickening polymers of the alkaline composition of step b) is in the range of 0.1% to 10% by weight, preferably 0.5% to 5% by weight, more preferably in the range of 1% to 3% by weight, calculated to the total of the alkaline composition of step b).

Viscosity of the Composition of Step b)

The skilled person suitably selects the concentration of the thickening polymer to yield the viscosity of a thickened gel.

The lower limit of viscosity suitably is 5,000 mPas or more, preferably 10,000 mPas or more to yield a sufficiently thickened product that does not drip from keratin fibers during processing.

The upper limit of viscosity suitably is 50,000 mPas or less, preferably 40,000 mPas or less to yield a product which may easily be applied onto keratin fibers.

To attain the above mentioned effects, the viscosity of the composition of step b) preferably is in the range of 5,000 mPas to 50,000 mPas, more preferably in the range of 10,000 mPas to 50,000 mPas, measured at 25° C. with a Brookfield viscometer and an appropriate spindle under atmospheric conditions.

Organic Solvents

The composition of step b) comprises one or more organic solvent(s) having two or more hydroxyl groups, from the viewpoint of softening/plasticizing the keratin fibers during heat processing as well as preventing too fast evaporation of the composition during the heating process.

Suitable organic solvent(s) having two or more hydroxyl groups are ethylene glycol, propylene glycol (1,2-propandiol), butylene glycol, dexpanthenol, and/or glycerol.

It is preferred that the composition of step b) comprises organic solvents at a total concentration in the range of 1% to 30% by weight, preferably 5% to 25% by weight, more preferably 7.5% to 20% by weight, calculated to the total of the composition of step b).

It is a further preferred aspect of the present invention that the composition of step b) comprises 1,2-propandiol at a total concentration in the range of 1% to 30% by weight, preferably 5% to 25% by weight, more preferably 7.5% to 20% by weight, calculated to the total of the composition of step b).

Surfactants of the Composition of Step b)

The non-reducing, non-oxidizing composition of step b) may comprise one or more surfactant(s) selected from non-ionic and/or anionic and/or cationic and/or zwitterionic and/or amphoteric surfactant(s), and/or their mixtures, from the viewpoint of emulsifying lipophilic compounds and/or enhancing spreadability of the composition onto keratin fibers.

Anionic Surfactants

Suitable anionic surfactants of the alkaline composition of step b) are selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures.

Suitable alkyl sulfate or preferably ethoxylated alkyl ether sulfate surfactant or mixtures thereof have an alkyl chain length of $C_{10}$ to $C_{22}$.

Suitable example foaming surfactants are laureth sulfates, coceth sulfate, pareth sulfate, capryleth sulphate, myreth sulfate, oleth sulfate, deceth sulfate, trideceth sulfate, coco sulphate, $C_{10}$-$C_{16}$ alkyl sulphate, $C_{11}$-$C_{15}$ alkyl sulphate, $C_{12}$-$C_{18}$ alkyl sulphate, $C_{12}$-$C_{15}$ alkyl sulphate, $C_{12}$-$C_{16}$ alkyl sulphate, $C_{12}$-$C_{13}$ alkyl sulfate, lauryl sulphate, myrystyl sulphate, palm kernel sulphate, cetearyl sulfate, cetyl sulphate, decyl sulphate, oleyl sulphate, behenyl sulphate and/or their salts. All of the aforementioned anionic surfactants may or may not be ethoxylated at various degrees.

Cations for the surfactants may be selected from sodium, potassium, magnesium and/or ammonium.

Further suitable anionic surfactants are alkyl ether carboxylates derived from alkanols having 6 to 22 carbon atoms, preferably one satisfying the following formula:

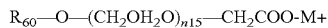

$R_{60}$—O—$(CH_2OH_2O)_{n15}$—$CH_2COO$-M+ wherein $R_{60}$ is an alkyl residue having 6 to 22 carbon atoms, n has a value in the range of 1 to 15, preferably 2 to 10, more preferably 2.5 to 7, and M+ is an appropriate cation, selected from the group consisting of an alkali metal, an alkaline earth metal, ammonium, an alkylammonium, an alkanolammonium or a glucammonium.

Particularly preferred are compounds of the above formula wherein R60 is an alkyl residue having 12 to 14 carbon atoms; n has a value in the range of 2.5 to 5 and M+ is an alkali metal cation such as sodium or potassium. Alkyl ether carboxylates are preferably used as liquid diluted aqueous solutions having a solid content lower than 30% by weight.

Alkyl ether carboxylates are obtained by ethoxylation and subsequent carboxymethylation of fatty alcohols.

Examples of commercially available alkyl ether carboxylate acid salts are marketed under the trade name AKYPO® by Kao Chemicals GmbH.

The most preferred anionic foaming surfactant is sodium lauryl sulfate.

Non-Ionic Surfactants

Suitable non-ionic surfactants of the alkaline composition of step b) are selected from alkyl polyglycosides, ethoxylated triglycerides, ethoxylated fatty alcohols, ethoxylated fatty acid esters, and/or their mixtures.

Suitable nonionic surfactants are alkyl polyglycosides according to the general structure:

$R_{23}O(R_{24}O)_tZ_x$

Wherein Z denotes a carbohydrate with $C_5$ to $C_6$, $R_{23}$ is an alkyl group with $C_8$ to $C_{18}$, $R_{24}$ is methyl, ethyl or propyl, t ranges from 0 to 10, and x ranges from 1 to 5.

Suitable compounds according to this structure are $C_9$-$C_{11}$ alkylpolyglycoside, the structures disclosed in EP-A 70 074, and JP 2015-123019A.

The preferred compounds according to the structure of above are decyl glucoside, lauryl glucoside, and coco glucoside, and the most preferred one is decyl glucoside.

Further suitable examples for non-ionic surfactants are N-alkylpolyhydroxyalkylamide type surfactants according to the following general formula:

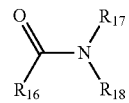

wherein $R_{16}$ is a linear or branched, saturated or unsaturated alkyl chain with $C_{11}$ to $C_{21}$, $R_{17}$ is linear or branched alkyl, or linear or branched hydroxyalkyl with $C_1$ to $C_4$, and $R_{18}$ is a linear or branched polyhydroxyalkyl chain with $C_3$ to $C_{12}$ and 3 to 10 hydroxyl groups.

Such compounds are disclosed in cosmetic compositions in WO96/27366 and their synthesis is disclosed in U.S. Pat. Nos. 1,985,424, 2,016,962, 2,703,798, and WO92/06984.

The preferred N-alkylpolyhydroxyalkylamide type surfactants have the following structure:

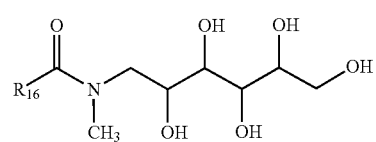

where $R_{16}$ has the same denotation as above for the general structure of N-alkylpolyhydroxyalkylamide type surfactants. The preferred surfactants as displayed above are known as N-methyl-N-acylglucamides.

The most preferred N-alkylpolyhydroxyalkylamide type surfactants are selected from lauroyl/myristoyl methyl glucamide and coco methyl glucamide.

Further suitable examples for non-ionic surfactants are ethoxylated fatty alcohol of the following general structure $$R_{25}(OCH_2CH_2)_{n4}OH$$

wherein $R_{25}$ is straight or branched, saturated or unsaturated alkyl chain which may be synthetic or natural with a C chain length in the range of 8 to 40, preferably 9 to 30 and more preferably 9 to 24 and n4 is a number in the range of 5 to 40, preferably 9 to 30.

Non-limiting suitable examples of the fatty alcohol ethoxylates are C9-11 Pareth-6, C9-11 Pareth-8, C9-15 Pareth-8, C11-13 Pareth-9, C11-13 Pareth-10, C11-15 Pareth-5, C11-15 Pareth-7, C11-15 Pareth-9, C11-15 Pareth-12, C11-15 Pareth-15, C11-15 Pareth-20, C11-15 Pareth-30, C11-15 Pareth-40, C11-21 Pareth-10, C12-13 Pareth-5, C12-13 Pareth-6, C12-13 Pareth-7, C12-13 Pareth-9, C12-13 Pareth-10, C12-13 Pareth-15, C12-13 Pareth-23, C12-14 Pareth-5, C12-14 Pareth-7, C12-14 Pareth-9, C12-14 Pareth-11, C12-14 Pareth-12, C12-15 Pareth-5, C12-15 Pareth-7, C12-15 Pareth-9, C12-15 Pareth-10, C12-15 Pareth-11, C12-15 Pareth-12, C12-16 Pareth-5, C12-16 Pareth-7, C12-16 Pareth-9, C13-15 Pareth-21, C14-15 Pareth-7, C14-15 Pareth-8, C14-15 Pareth-11, C14-15 Pareth-12, C14-15 Pareth-13, C20-22 Pareth-30, C20-40 Pareth-10, C20-40 Pareth-24, C20-40 Pareth-40, C20-40 Pareth-95, C22-24 Pareth-33, Beheneth-5, Beheneth-10, Beheneth-15, Beheneth-20, Beheneth-25, Beheneth-30, Ceteareth-5, Ceteareth-6, Ceteareth-7, Ceteareth-10, Ceteareth-11, Ceteareth-12, Ceteareth-15, Ceteareth-20, Ceteareth-25, Ceteareth-30, Ceteareth-35, Ceteareth-40, Laureth-5, Laureth-10, Laureth-15, Laureth-20, Laureth-25, Laureth-30, Laureth-40, Myreth-5, Myreth-10, Ceteth-5, Ceteth-10, Ceteth-15, Ceteth-20, Ceteth-25, Ceteth-30, Ceteth-40, Oleth-5, Oleth-10, Oleth-15, Oleth-20, Oleth-25, Oleth-30, Oleth-40, Steareth-5, Steareth-10, Steareth-15, Steareth-20, Steareth-25, Steareth-30, Steareth-35, and Steareth-40. They may also be comprised in the compositions as a mixture of more than one surfactant.

Further suitable nonionic surfactants are polypropylene glycol ethers of fatty alcohol according to general structure $$R_{25}(OCH_2—CH_2—CH_2)_{n5}OH$$

wherein $R_{25}$ is straight or branched, saturated or unsaturated fatty alcohol which may be synthetic or natural with a C chain length in the range of 8 to 40, preferably 9 to 30 and more preferably 9 to 24 and n5 is a number in the range of 1 to 40, preferably 3 to 30.

Suitable non-limiting examples are PPG-3 Caprylyl ether, PPG-5 Caprylyl ether, PPG-10 Caprylyl ether, PPG-10 Cetyl ether, PPG-20 Cetyl ether, PPG-28 Cetyl ether, PPG-30 Cetyl ether, PPG-7 Lauryl ether, PPG-10 Lauryl ether, PPG-10 Oleyl ether, PPG-20 Oleyl ether, PPG-23 Oleyl ether, PPG-30 Oleyl ether, PPG-11 Stearyl ether and PPG-15 Stearyl ether.

Further suitable nonionic surfactants are polyethylene glycol fatty acid esters of the following general structure $$R_{26}C(O)(OCH_2CH_2)_{n6}OH$$

wherein $R_{26}$ is straight or branched, saturated or unsaturated alkyl group which may be synthetic or natural with a C chain length in the range of 7 to 39, preferably 9 to 29 and more preferably 9 to 23 and n6 is a number in the range of 5 to 40, preferably 9 to 30.

Suitable non-limiting examples are PEG-8 Behenate, PEG-8 Caprate, PEG-8 Caprylate, PEG-5 Cocoate, PEG-8 Cocoate, PEG-9 Cocoate, PEG-10 Cocoate, PEG-15 Cocoate, PEG-6 Isopalmitate, PEG-6 Isostearate, PEG-8 Isostearate, PEG-9 Isostearate, PEG-10 Isostearate, PEG-12 Isostearate, PEG-20 Isostearate, PEG-30 Isostearate, PEG-40 Isostearate, PEG-6 Laurate, PEG-8 Laurate, PEG-9 Laurate, PEG-10 Laurate, PEG-12 Laurate, PEG-14 Laurate, PEG-20 Laurate, PEG-30 Laurate, PEG-8 Myristate, PEG-20 Myristate, PEG-5 Oleate, PEG-6 Oleate, PEG-7 Oleate, PEG-8 Oleate, PEG-9 Oleate, PEG-10 Oleate, PEG-11 Oleate, PEG-12 Oleate, PEG-15 Oleate, PEG-20 Oleate, PEG-30 Oleate, PEG-32 Oleate, PEG-6 Palmitate, PEG-18 Palmitate, PEG-20 Palmitate, PEG-5 Stearate, PEG-6 Stearate, PEG-7 Stearate, PEG-8 Stearate, PEG-9 Stearate, PEG-10 Stearate, PEG-12 Stearate, PEG-14 Stearate, PEG-15 Stearate, PEG-20 Stearate, PEG-25 Stearate, PEG-30 Stearate, PEG-35 Stearate and PEG-40 Stearate.

Further suitable nonionic surfactants are propoxylated fatty acid esters of the following general structure $$R_{27}C(O)(OCH_2—CH_2—CH_2)_{n8}OH$$

wherein $R_{27}$ is straight or branched, saturated or unsaturated alkyl group which may be synthetic or natural with a C chain length in the range of 7 to 39, preferably 9 to 29 and more preferably 9 to 23 and n8 is a number in the range of 1 to 40, preferably 9 to 30.

Suitable non-limiting examples are PPG-15 Isostearate, PPG-9 Laurate, PPG-26 Oleate and PPG-36 Oleate.

Further suitable nonionic surfactants are ethoxylated and propoxylated fatty alcohols of the following general structure $$R_{28}(OCH_2—CH_2—CH_2)_{n9}(OCH_2CH_2)_{n10}OH$$

wherein $R_{28}$ is straight or branched, saturated or unsaturated alkyl group which may be synthetic or natural with a C chain length in the range of 7 to 39, preferably 9 to 29 and more preferably 9 to 23 and n9 and n10 may be the same or different and are a number in the range of 1 to 40.

Further suitable nonionic surfactants are ethoxylated triglycerides. Well-known and commonly used examples are ethoxylated castor oil such as PEG-40 hydrogenated castor oil or and PEG-60 hydrogenated castor oil.

The preferred non-ionic surfactant(s) are selected from alkyl polyglycoside(s), ethoxylated and/or propoxylated fatty alcohols, ethoxylated and/or propoxylated triglycerides, ethoxylated and/or propoxylated fatty alcohols, ethoxylated or propoxylated fatty acid esters, N-alkylpolyhydroxyalkylamides, preferably they are selected from $C_8$-$C_{22}$ alkyl polyglycoside(s), more preferably they are selected from decyl glucoside, lauryl glucoside, and coco glucoside, and further more preferably it is coco glucoside.

Cationic Surfactants

Suitable cationic surfactants are of quaternary ammonium structure according to the following general structure $$R_{32}—\overset{\overset{R_{33}}{|}}{\underset{\underset{R_{31}}{|}}{N^+}}—R_{30} \quad X^-$$

where $R_{30}$ is a saturated or unsaturated, branched or linear alkyl chain with $C_8$-$C_{22}$ or $$R_{34}CONH(CH_2)_n$$

where $R_{34}$ is saturated or unsaturated, branched or linear alkyl chain with $C_7$-$C_{21}$ atoms and n has typical value of 1-4 or

where $R_{35}$ is saturated or unsaturated, branched or linear alkyl chain with $C_7$-$C_{21}$ atoms and n has typical value of 1-4, and $R_{31}$ is unsaturated or saturated, branched or linear alkyl chain with $C_1$-$C_{22}$ atoms or

or

where $R_{34}$, $R_{35}$ and n are same as above.

$R_{32}$ and $R_{33}$ have an alkyl chain with $C_1$ to $C_4$, and $X^-$ is typically chloride, bromide, or methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimethyl ammonium chloride, dioleoylethyl dimethyl ammonium methosulfate, dioleoylethyl hydroxyethylmonium methosulfate, behenyl trimethyl ammonium chloride, and/or their mixtures.

Suitable cationizable surfactants are surfactants which carry one or more chemical group(s) that is/are at least at some point non-ionic at pH above 7, but which is/are positively charged at a pH under 7. Such groups are, for example, primary, secondary, and tertiary amino groups. It is well known to the skilled reader that the aforementioned groups are becoming ammonium groups at a pH below 7.

Suitable cationizable surfactants are, for example, according to the following general structure

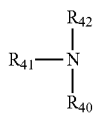

where $R_{40}$ is a saturated or unsaturated, straight or branched alkyl chain, optionally modified with ethoxylate and/or propxylate groups, with $C_{12}$ to $C_{22}$, $R_{41}$ is selected from H or straight or branched alkyl with $C_1$ to $C_4$, and $R_{42}$ is selected from H or straight or branched alkyl with $C_1$ to $C_4$.

Suitable compounds according to this structure are, for example, dodecylamine, tridecylamine, tetradecylamine, pentadecylamine, stearylamine, octylamine, oleylamine, behenylamine, stearyl methylamine, stearyl dimethylamine, octyl methylamine, octyl dimethylamine, behenyl methylamine, behenyl dimethylamine, stearyl ethylamine, stearyl ethylamine, octyl ethylamine, octyl ethylamine, behenyl ethylamine, behenyl ethylamine, stearyl propylamine, stearyl dipropylamine, octyl propylamine, octyl dipropylamine, behenyl propylamine, behenyl dipropylamine and/or their salts and/or their mixtures. The aforementioned compounds may be modified with ethoxylate and/or propoxylate groups.

Further suitable cationizable surfactants are known as alkyl amido alkyl amine surfactants and/or their salt(s) and are according to the following general structure

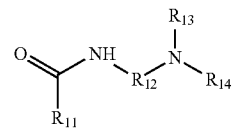

where $R_{11}$ is a saturated or unsaturated, straight or branched alkyl chain with $C_{11}$ to $C_{21}$, $R_{12}$ is a straight or branched alkyl chain with $C_1$ to $C_6$, $R_{13}$ and $R_{14}$ may be the same of different selected from H and straight or branched alkyl chain with $C_1$ to $C_4$.

Suitable compounds according to this definition are, for example, cocamidopropyl dimethylamine, stearamidopropyl dimethylamine, behenamidopropyl dimethylamine, and/or their salt(s).

Amphoteric/zwitterionic Surfactants

Suitable amphoteric/zwitterionic surfactants may be selected from compounds according to the general structure(s)

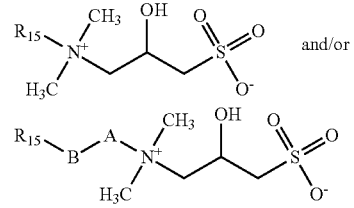

and/or wherein $R_{15}$ is a straight or branched, saturated or unsaturated, substituted or unsubstituted alkyl chain with a carbon number of $C_{10}$ to $C_{22}$, preferably $R_{15}$ is a straight alkyl chain with a carbon number of $C_{10}$ to $C_{16}$, A is a straight alkyl chain with a carbon number of $C_1$ to $C_6$ or a branched alkyl chain with a carbon number of $C_3$ to $C_6$, preferably A is a linear alkyl chain with a carbon number of $C_3$, and B is an amide or an ester group.

Suitable compounds are known as hydroxysultaine surfactants, such as cocoamidopropyl hydroxysultaine, laurylamidopropyl hydroxysultaine, erucamidopropyl hydroxysultaine, lauryl hydroxysultaine, and cocoyl hydroxysultaine, and/or their salt(s).

Further suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

The preferred amphoteric/zwitterionic surfactant(s) is/are selected from alkylamido betaines and/or alkylamidoalkyl betaine surfactants.

Surfactant Concentration

The total lower concentration of surfactants in the alkaline composition of step c) is in the range of 0.1% by weight or more, preferably 0.5% by weight or more, more preferably 0.75% by weight or more, calculated to the total of the composition of step b), form the viewpoint of generating sufficient amount of foam.

The total upper concentration of surfactants in the alkaline composition of step c) is in the range of 10% by weight or less, preferably 8% by weight or less, more preferably 5% by weight or less, calculated to the total of the composition of step c), from the viewpoint of generating a foam, which is dispensable from the foam dispenser.

For attaining the above-mentioned effects, the total concentration of surfactants in the alkaline composition of step b) is in the range of 0.1% to 10% by weight, preferably 0.5% to 8% by weight, more preferably 0.75% to 5% by weight, calculated to the total of the composition of step c).

Viscosity of the Composition

It is preferred from the viewpoint of applicability to the customer's hair that the viscosity of the composition of step b) is in the range of 100 to 2,000 mPas, preferably 200 to 1,500 mPas, more preferably 500 to 1,000 mPas.

The viscosity of the composition may be adjusted by all means available to the skilled person. Such means include the addition of a thickening polymer, preferably an acrylate-based thickening polymer, addition of organic solvents.

The skilled person may also make use of all of the aforementioned options to adjust the viscosity of the composition.

Moisture Barrier of Step c)

Preferably the moisture barrier of step c) is a foil or wrap impermeable for water vapor, or housing made of a material impermeable for water vapor, with the provision that the selected materials for the moisture barrier are heat resistant up to the selected process temperature.

In principle, many materials are suitable for serving as moisture barrier such as aluminum foil, plastic foil, and/or plastic device which enclose the curler and/or hair streak. Alternatively, certain types of anti-flammable fabric is equally suitable. The purpose of the moisture barrier is to keep the hair moist over the total processing time of heating.

Suitable examples are re-sealable zipper storage bags made of materials such a slow density polyethylene.

For the purpose of the present invention, it is one aspect to cover the keratin fibers with the moisture barrier. In another aspect the hair is not covered with a moisture barrier.

Winding and Heating Process

It is preferred form the viewpoint of convenience that for process step a) the hair is put under mechanical tension on a curler or roller having heating means. After completion of step d) the curler may then be connected to a digital perm machine for heating the curler and the hair.

It is preferred from the viewpoint of minimizing hair damage that the hair is heating in step d) in the range of 80° C. to 180° C., preferably 85° C. to 140° C., more preferably 90° C. to 120° C.

From the viewpoint of having a short processing time and a speedy hair treatment, the heating time of step d) preferably is in the range of 2 min to 45 min, preferably in the range of 5 min to 30 min, more preferably in the range of 5 min to 20 min.

Optional Ingredients of the Composition of Step b)

The non-reducing, non-oxidizing alkaline composition of step b) may further comprise cationic polymers, amino acids, UV filters, any type of hair dyes.

Particularly preferred are cationic polymers such as the ones known under their CTFA name Polyquaternium, for example Polyquaternium 6, Polyquaternium 10, Polyquaternium 16, and Polyquaternium 37.

Preferably, the concentration of cationic polymers in the composition is in the range of 0.01% by weight to 1% by weight, calculated to the total weight of the composition.

The following examples are to illustrate the present invention, but not to limit it.

EXAMPLES

Example 1

The following compositions were prepared by conventional formulation and mixing techniques:

| Ingredients | Inventive comp. 1 [% by weight] | Inventive comp. 2 [% by weight] | Inventive comp. 3 [% by weight] |
|---|---|---|---|
| Ammonia solution (25%) | 10.0 | 10.0 | 10.0 |
| 1,2-propandiol | 10.0 | 10.0 | 10.0 |
| Carbopol 980 NF (acrylates homopolymer) | 2.0 | — | — |
| Natrosol 250 HX (Hydroxyethyl-celllose) | — | 2.0 | — |
| Cosmedia Ultragel 300 (Polyquaternium-37) | — | — | 2.0 |
| Water | Ad 100.0 | | |

The pH of compositions was 10.0. The viscosities ranged between 20,000 mPas and 40,000 mPas.

Human hair streaks (Caucasian, 21 cm long, 2 g per bundle) were purchased from Fischbach+Miller Haar, Laupheim, Germany. The hair streaks were shampooed with a commercially available shampoo under the brand name Goldwell Deep Cleansing Shampoo. Then the streaks were towel dried. Then 1 g of the compositions from above was applied to the hair streaks with a brush. The streaks were then winded on perming rods possessing an electrical heating system. Prior to heating, each of the rods were covered with a plastic bag (commercial re-sealable zipper storage bag) made of low-density polyethylene. The rods were then heated to a temperature in the range of 90° C. to 110° C. for 20 min with a digital perming machine. Then the rods were allowed to cool down, the plastic bag was removed, and the hair was shampooed with the same shampoo from above. The streaks were then blow-dried.

Assessment of curling efficiency was investigated by measuring and calculating the curl ratio L according to the formula:

$$L=(L_0-L_t)/L_0$$

wherein $L_0$ is the length of the hair streak prior to curling and $L_t$ is the length of the hair streak after the curling experiment. The number is reported as percentage and a higher percentage corresponds to higher curling degree.

The table below reports the experimental results:

| Parameter | Inventive comp. 1 | Inventive comp. 2 | Inventive comp 3 |
|---|---|---|---|
| Curl ratio | 13.6 | 18.2 | 18.2 |

As a result it was found that the inventive compositions showed strong curling ratios.

Moreover, the compositions were easy to apply and remained on the hair streak during processing.

The following examples are within the scope of the present invention.

Example 2

The composition of step b) is as follows:

|  | % by weight |
|---|---|
| Ammonia solution (25%) | 2.5 |
| 1,2-propandiol | 10.0 |
| Acrylates copolymer* | 0.5 |
| Sodium laureth sulfate (1-5 EO) | 3.0 |
| Water | ad 100.0 |

*Acrylates/c10-30 alkyla crylate crosspolymer

The pH of the composition is in the range of 8 to 10 and may be adjusted with HCl.

Example 3

The composition of step b) is as follows:

|  | % by weight |
|---|---|
| Ammonia solution (25%) | 2.5 |
| Monoethanolamine | 0.25 |
| 1,2-propandiol | 10.0 |
| Hydroxypropyl starch | 0.5 |
| Coco glucoside | 0.5 |
| Water | ad 100.0 |

The pH of the composition is in the range of 8 to 11 and may be adjusted with HCl.

Example 4

The composition of step b) is as follows:

|  | % by weight |
|---|---|
| Ammonia (25%) | 1.5 |
| 1,2-propandiol | 5.0 |
| Aminomethyl propanol | 0.5 |
| Cetrimoniumchloride | 2.0 |
| Cocoyl betaine | 1.0 |
| Xanthan gum | 2.0 |
| Water | ad 100.0 |

The pH of the composition is in the range of 9 to 10 and may be adjusted with HCl.

The invention claimed is:

1. A process for perming keratin fibers comprising:
  a) putting keratin fibers under mechanical tension on a curler or a roller,
  b) applying a non-reducing, non-oxidizing alkaline composition onto the keratin fibers, wherein the non-reducing, non-oxidizing alkaline composition has a pH ranging from 7 to 12, a viscosity ranging from at least 10,000 mPas and no more than 40,000 mPas, and comprises:
    i) one or more alkalizing agents at a total concentration ranging from 0.1% to 10% by weight, calculated to a total weight of the non-reducing, non-oxidizing alkaline composition, wherein the one or more alkalizing agents comprise at least one selected from: ammonia and/or its salts; and aminomethyl propanol, monoethanolamine, diethanolamine, tris-(hydroxymethyl)-aminomethane, and/or at least one of their salts,
    ii) one or more thickening polymers at a total concentration ranging from 1% to 3% by weight, calculated to the total weight of the non-reducing, non-oxidizing alkaline composition, wherein the one or more thickening polymers comprise a thickening polymer selected from the group consisting of:
      an acrylate anionic thickening polymer or a mixture of one or more acrylate anionic thickening polymers, wherein the one or more acrylic polymers are selected group consisting of acrylates/c10-30 alkyl acrylate crosspolymer, acrylates/steareth-20 methacrylate copolymer, acrylates/stearyl acrylate/dimethicone methacrylate copolymer, acrylates/beheneth-25 methacrylate copolymer, and acrylates/lauryl acrylate/stearyl acrylate/ethylamine oxide methacrylate copolymer;
      a non-ionic thickening polymer selected from the group consisting of methyl cellulose, ethyl cellulose, hydroxyethylcellulose, methylhydroxyethylcellulose, methylhydroxypropylcellulose, and a mixture thereof;
      a cationic thickening polymer selected from the group consisting of Polyquaternium 6, Polyquaternium 16, Polyquaternium 37 and a mixture thereof;
      and a non-associative anionic thickening polymer or a mixture of one or more non-associative anionic thickening polymers are selected from the group consisting of xanthan gum, dehydroxanthan gum, starch, and hydrophobically modified starch,
    iii) one or more organic solvents having two or more hydroxyl groups at a total concentration ranging from 5% to 10% by weight, calculated to the total weight of the non-reducing, non-oxidizing alkaline composition, wherein the one or more organic solvents having two or more hydroxyl groups are selected from 1,2-propandiol, butylene glycol, and/or glycerol, and
    iv) a remainder component of the non-reducing, non-oxidizing alkaline composition comprising water,
  c) optionally covering the keratin fibers with a moisture barrier,
  d) heating the keratin fibers to a temperature ranging from 50° C. to 230° C.,
  e) optionally removing the moisture barrier from the keratin fibers,
  f) releasing tension from the keratin fibers, and
  g) optionally rinsing-off the keratin fibers, wherein a) and b) are executable in either order and/or f) and g) are executable in either order.

2. The process according to claim 1, wherein the keratin fibers are heated according to d) to a temperature ranging from 80° C. to 180° C.

3. The process according to claim 1, wherein the heating time of d) ranges from 2 min to 45 min.

4. The process according to claim 1, wherein, for a), the curler or the roller have heating means.

5. The process according to claim 1, wherein the moisture barrier of c) is a foil or wrap impermeable for water vapor, or housing made of a material impermeable for water vapor, with the provision that selected materials for the moisture barrier are heat resistant up to the temperature of 230° C.

6. The process according to claim 1, wherein the one or more organic solvents having two or more hydroxyl groups are selected from 1,2-propandiol and glycerol.

7. The process according to claim 1, wherein the water is present at a total concentration of at least 67% by weight, calculated to the total weight of the non-reducing, non-oxidizing alkaline composition.

8. The process according to claim 1, comprising two or more thickening polymers.

* * * * *